(12) United States Patent
Giordano et al.

(10) Patent No.: US 7,696,219 B2
(45) Date of Patent: Apr. 13, 2010

(54) METHOD AND COMPOSITION FOR SUPPLEMENTATION OF NUTRITIONAL DEFICIENCIES IN RENAL PATIENTS

(75) Inventors: John A. Giordano, West Orange, NJ (US); Charles J. Balzer, Lavalette, NJ (US)

(73) Assignee: Everett Laboratories, Inc., West Orange, NJ (US)

( * ) Notice: Subject to any disclaimer, the term of this patent is extended or adjusted under 35 U.S.C. 154(b) by 1580 days.

(21) Appl. No.: 10/964,754

(22) Filed: Oct. 15, 2004

(65) Prior Publication Data

US 2005/0100613 A1 May 12, 2005

Related U.S. Application Data

(63) Continuation-in-part of application No. 09/671,283, filed on Sep. 27, 2000, now Pat. No. 6,995,166.

(51) Int. Cl.
- A61K 31/34 (2006.01)
- A61K 31/355 (2006.01)
- A61K 31/44 (2006.01)
- A61K 31/51 (2006.01)
- A61K 47/00 (2006.01)
- A61K 33/32 (2006.01)
- A61K 33/04 (2006.01)

(52) U.S. Cl. .......... 514/276; 514/256; 514/348; 514/458; 514/474; 424/439; 424/641; 424/702

(58) Field of Classification Search .......... 514/276, 514/256, 458, 474, 348; 424/439
See application file for complete search history.

(56) References Cited

U.S. PATENT DOCUMENTS

| | | | |
|---|---|---|---|
| 3,160,564 A | 12/1964 | Hanus | |
| 4,357,343 A | 11/1982 | Madsen et al. | |
| 4,710,387 A | 12/1987 | Uiterwaal et al. | |
| 4,740,373 A | 4/1988 | Kesselman et al. | |
| 4,804,535 A | 2/1989 | Kesselman et al. | |
| 4,940,658 A | 7/1990 | Allen et al. | |
| 4,945,083 A | 7/1990 | Jansen, Jr. | |
| 4,957,938 A | 9/1990 | Anderson et al. | |
| 5,093,143 A | 3/1992 | Behr et al. | |
| 5,108,767 A | 4/1992 | Mulchandani et al. | |
| 5,278,329 A | 1/1994 | Anderson | |
| 5,374,560 A | 12/1994 | Allen et al. | |
| 5,438,017 A | 8/1995 | Allen et al. | |
| 5,457,055 A | 10/1995 | Allen et al. | |
| 5,494,678 A | 2/1996 | Paradissis et al. | |
| 5,514,382 A | 5/1996 | Sultenfuss | |
| 5,556,644 A | 9/1996 | Chandra | |
| 5,563,126 A | 10/1996 | Allen et al. | |
| 5,626,884 A | 5/1997 | Lockett | |
| 5,728,678 A | 3/1998 | Trimbo et al. | |
| 5,795,873 A | 8/1998 | Allen | |
| 5,869,084 A | 2/1999 | Paradissis et al. | |
| 5,898,036 A | 4/1999 | McLeod | |
| 5,922,704 A | 7/1999 | Bland | |
| 5,976,568 A * | 11/1999 | Riley | 424/451 |
| 6,042,849 A | 3/2000 | Richardson et al. | |
| 6,048,846 A | 4/2000 | Cochran | |
| 6,054,128 A * | 4/2000 | Wakat | 424/765 |
| 6,090,414 A | 7/2000 | Passwater et al. | |
| 6,103,756 A | 8/2000 | Gorsek | |
| 6,136,859 A | 10/2000 | Henriksen | |
| 6,207,651 B1 | 3/2001 | Allen et al. | |
| 6,228,388 B1 | 5/2001 | Paradissis et al. | |
| 6,297,224 B1 | 10/2001 | Allen et al. | |
| 6,528,496 B1 | 3/2003 | Allen et al. | |
| 6,995,166 B1 * | 2/2006 | Giordano et al. | 514/276 |

FOREIGN PATENT DOCUMENTS

| | | |
|---|---|---|
| EP | 0 482 715 | 4/1992 |
| EP | 0 891 719 | 1/1999 |
| WO | 99/07419 | 2/1999 |

OTHER PUBLICATIONS

Dietary Reference Intake for thiamin, roboflavin, niacin, vitamin B6, folate, vitamin B12, pantothenic acid, biotin and cholin, National Academy Press, Washington D.C. 1998, pp. 306-352.*
Stein et al., "3 Blood Purification", pp. 52-62 (1985).
Centrum, From A to zinc, www.centrum.com/multi/centrum.asp, marketed since 1978.
GNC Ultra Mega Green, GNC Vitamins and minerals, gnc. mondosearch.com.
Nephrology Dialysis Transplantation (1998) 13 [Suppl 2]: 23-27.

(Continued)

*Primary Examiner*—Shengjun Wang
(74) *Attorney, Agent, or Firm*—Sheppard, Mullin, Richter & Hampton LLP

(57) ABSTRACT

The present invention relates to compositions and methods for treating the nutritional deficiencies observed in patients suffering from renal disease and associated disorders. Specifically, the method involves administering to a renal patient a composition comprising vitamin C, vitamin E, B-complex vitamins, selenium, and zinc.

6 Claims, No Drawings

OTHER PUBLICATIONS

Holben and Smith, 99(7) *Journal of the American Dietetic Assoc.*, pp. 836-843 (1999).
Ponka and Kuhlback, 213, *Acta. Med. Scand.*, pp. 305-307 (1983).
Anderson et al., 54 *Am. J. Clin. Nutr.*, pp. 909-916 (1991).
British Medical Journal, Hypervitaminosis A Accompanying Advanced Chronic Renal Failure (1975).
Burton and Ingold, "Vitamin E as an In Vitro and In Vivo Antioxidant", pp. 7-22.
Burk, "3 Biological Activity of Selenium", pp. 53-70 (1983).
Rolton et al., "6 Nephrol. Dialysis Transplant", pp. 440-443 (1991).
Ono, "26(5) Clinical Nephrology", pp. 239-243 (1986).
Hultberg et al., "40(4) Clinical Nephrology", pp. 230-234 (1993).
Ono, "40 Vitamin E Supplementation in Anemia", pp. 440-445 (1985).
Parfrey, "23 Advances in Nephrology", pp. 311-330 (1994).
Lacour, "127 Clinica Chimica Acta", pp. 205-215 (1983).
Allman et al., "150 The Medical Journal of Australia", pp. 130-133.
Vincent, "The Biochemistry of Chromium", pp. 715-718.
Fraker et al., "Link Between Immune Status and Zinc Status", pp. 1399S-1460S.
Fukagawa et al., "21 Mineral Electrolyte Metab", pp. 97-100 (1995).
Islam et al., "150 Astherosclerosis", pp. 217-224 (2000).
Hoogeveen, "Hyperhomocysteinemia, Type 2 Diabetes, and Mortality", pp. 1506-1511.
Moustapha, "Homocysteine and Renal Failure", pp. 138-141.
Robinson et al., "94(11) Circulation", pp. 2743-2748 (1996).
Jungers et al., "14 Nephrol. Dialysis Transplant", pp. 2903-2906 (1996).
Arnadottir et al., "15 Nephrol. Dialysis Transplant", pp. 524-528 (1999).
Janssen et al., "22 Miner Electrolyte Metab.", pp. 110-114 (1996).
Bostom et al., "49 Kidney International", pp. 147-152 (1996).
Oishi et al., "15 Nephrol. Dialysis Transplant", pp. 851-855 (2000).
Perna et al., "25 Mineral and Electrolyte Metabolism", pp. 95-99 (1999).
Bogye et al., "84 Nephron", pp. 119-123 (2000).
Kornatowska et al., "13 Nephrology Dialysis Transplantation", pp. 2829-2832 (1998).

* cited by examiner

METHOD AND COMPOSITION FOR SUPPLEMENTATION OF NUTRITIONAL DEFICIENCES IN RENAL PATIENTS

The present application is a continuation-in-part, and claims the benefit under 35 U.S.C. § 120, of U.S. patent application Ser. No. 09/671,283 filed Sep. 27, 2000, now U.S. Pat. No. 6,995,166 which is expressly incorporated fully herein by reference.

FIELD OF THE INVENTION

The present invention relates to compositions comprising various vitamins and minerals, and methods for using these compositions for the treatment of renal disease and associated disorders.

BACKGROUND OF THE INVENTION

The kidney has three major physiological functions: excretory, endocrine, and metabolic. However, regulation and excretion of water, minerals, and other nutrients is the most important function of the kidneys. Metabolic waste products eliminated by the kidneys include urea, creatinine, uric acid, hemoglobin degradation products, and hormone metabolites. The kidneys also play a role in arterial pressure regulation by secreting vasoactive substances such as renin. In addition, the kidneys secrete erythropoietin, which stimulates red blood cell production, and produce 1,25-dihydroxy vitamin $D_3$, the active form of vitamin D. Any of these functions may be impaired in renal disease leading to disruptions in the nutritional status of the patient. TEXTBOOK OF MEDICAL PHYSIOLOGY 315 (Guyton & Hall, $9^{th}$ ed. 1996).

Renal disease is one of the leading causes of morbidity, with millions of individuals affected annually. Generally, renal disease may be classified into two categories: 1) acute renal failure and 2) chronic renal failure. Acute renal failure is characterized by a sudden reduction or cessation of renal function. In contrast, chronic renal failure refers to a progressive loss of renal function, usually a result of an underlying pathological condition. For example, immunological disorders such as lupus erythematosus, metabolic disorders such as diabetes mellitus and hypertension, and infectious diseases such as tuberculosis can lead to chronic renal failure. As renal function continues to deteriorate, patients develop end-stage renal failure (ESRD) that eventually requires dialysis treatment or transplantation. Id. at 413.

Patients with chronic renal failure typically develop generalized edema, acidosis, and uremia, an accumulation of nitrogenous metabolites in the blood. To alleviate these symptoms, patients are placed on dietary therapy or dialysis. The protein-restricted diet prescribed for renal patients is generally deficient in vitamins such as folate, the B vitamins, and vitamin C. HANDBOOK OF NUTRITION AND THE KIDNEY 42 (Mitch & Klahr, eds., $3^{rd}$ ed. 1998) (hereinafter "HANDBOOK"). In addition, the dialysis procedure itself may remove vitamins and nutrient compounds. Gastrointestinal absorption of vitamins may be also altered in patients suffering from chronic renal failure. Makoff, 25 MINER. ELECTROLYTE METABOL. 349-351 (1999).

Compliance with the restrictive renal diet may also result in deficiencies in trace minerals such as zinc and selenium. Highly protein-bound minerals may be lost in excessive amounts in patients with proteinuria. Zima et al., 17 BLOOD PURIF. 182-186 (1999). Furthermore, it has been shown that plasma levels of selenium are decreased in dialysis patients. HANDBOOK, at 43. Poor nutritional status and insufficient levels of vitamins and minerals may place renal patients at higher risk for diseases such as anemia, infections, and cardiovascular disease, or aggravate pre-existing conditions such as hyperlipidemia, osteoporosis, and viral hepatitis. MODERN NUTRITION IN HEALTH AND DISEASE, 1447 (Shils et al., eds., $9^{th}$ ed. 1999).

Nutritional intervention is critical to the management of chronic renal disease and end-stage renal disease. Dietary therapy should maintain or improve the nutritional status of the renal patient and minimize or prevent uremic and metabolic toxicities associated with renal failure. The challenge is to simplify a complex dietary regimen while providing an effective nutritional treatment. The nutritional compositions and related methods described herein include the numerous vitamins and minerals deficient in the restricted diet of the renal patient. Thus, the compositions and methods of the present invention offer to meet the nutritional needs of the renal patient in an uncomplicated approach.

SUMMARY OF THE INVENTION

The present invention provides nutritional compositions and methods of using these compositions for treating patients with renal disease. Specifically, the present invention discloses novel compositions of vitamins and minerals in an amount that can be used to supplement the nutritional deficiencies observed in patients afflicted with renal disease, renal insufficiency, or end-stage renal disease. The compositions of the present invention can also be used as nutritional supplements for patients undergoing dialysis therapy or for patients on a restricted diet. In addition, the compositions can be used to treat the nutritional deficiencies of any disease state that results in increased oxidative stress, elevated cholesterol levels, or elevated homocysteine levels.

The compositions of the present invention comprise numerous vitamins and minerals that will improve the nutritional state of a patient. The vitamins included in the compositions of the present invention may include vitamin C, vitamin E, vitamin $B_1$, vitamin $B_2$, vitamin $B_3$, vitamin $B_5$, vitamin $B_6$, vitamin $B_{12}$, biotin, and vitamin $B_9$. The minerals included in the compositions of the present invention may include selenium and zinc.

In one embodiment of the present invention, the compositions may comprise one or more of vitamin C in the form of ascorbic acid; vitamin E in the form of d-alpha tocopheryl succinate or d-alpha tocopheryl acetate; vitamin $B_1$ in the form of thiamine mononitrate; vitamin $B_2$ in the form of riboflavin; vitamin $B_3$ in the form of niacinamide or niacin; vitamin $B_5$ in the form of pantothenic acid (d-calcium pantothenate); vitamin $B_6$ in the form of pyridoxine hydrochloride; vitamin $B_{12}$ in the form of cyanocobalamin; biotin; vitamin $B_9$ in the form of folic acid, folacin, metafolin, folate and/or one or more natural isomers of folate including (6S)-tetrahydrofolic acid or a polyglutamyl derivative thereof, 5-methyl-(6S)-tetrahydrofolic acid or a polyglutamyl derivative thereof, 5-formyl-(6S)-tetrahydrofolic acid or a polyglutamyl derivative thereof, 10-formyl-(6R)-tetrahydrofolic acid or a polyglutamyl derivative thereof, 5,10-methylene-(6R)-tetrahydrofolic acid or a polyglutamyl derivative thereof, 5,10-methenyl-(6R)-tetrahydrofolic acid or a polyglutamyl derivative thereof and 5-formimino-(6S)-tetrahydrofolic acid or a polyglutamyl derivative thereof; selenium in the form of L-selenomethionine; and zinc in the form of L-Optizinc ZML-200 InterHealthθ™ or zinc oxide.

In another embodiment of the present invention, the compositions may be substantially free of any other added vitamins and minerals not described in the preceding paragraph.

For example, the compositions of the present invention may be substantially free of added alpha carotene; substantially free of added beta carotene; substantially free of added lutein; substantially free of added lycopene; substantially free of added zeaxanthin; substantially free of added vitamin $B_4$; substantially free of added vitamin $B_7$; substantially free of added vitamin $B_8$; substantially free of added vitamin $B_{10}$; substantially free of added vitamin $B_{11}$; substantially free of added vitamin D; substantially free of added calcium; substantially free of added chromium; substantially free of added iron; substantially free of added magnesium; substantially free of added copper; substantially free of added manganese; substantially free of added boron; substantially free of added odorless garlic; substantially free of added coenzyme Q-10; substantially free of added 1-carnitine; substantially free of added grape seed extract; substantially free of added green tea extract; substantially free of added quercetin; substantially free of added hawthorne berries; and/or substantially free of added alpha lipoic acid.

In another specific embodiment, the compositions of the present invention may be substantially free of added vitamin C; substantially free of added vitamin E; substantially free of added vitamin $B_1$; substantially free of added vitamin $B_2$; substantially free of added vitamin $B_3$; substantially free of added vitamin $B_5$; substantially free of added vitamin $B_6$; substantially free of added vitamin $B_{12}$; substantially free of added biotin; substantially free of added vitamin $B_9$; substantially free of added selenium; and/or substantially free of added zinc.

In another specific embodiment, the compositions may comprise about 60 mg to about 140 mg vitamin C; about 17.5 IU to about 52.5 IU vitamin E; about 1.5 mg to about 4.5 mg vitamin $B_1$; about 1 mg to about 3 mg vitamin $B_2$; about 10 mg to about 30 mg vitamin $B_3$; about 5 mg to about 15 mg vitamin $B_5$; about 18 mg to about 42 mg vitamin $B_6$; about 500 µg to about 1500 µg vitamin $B_{12}$; about 150 µg to about 450 µg biotin; about 3 mg to about 8 mg vitamin $B_9$; about 35 µg to about 105 µg selenium; and about 10 mg to about 30 mg zinc.

In another particular embodiment, the compositions of the present invention may comprise about 80 mg to about 120 mg vitamin C; about 28 IU to about 42 IU vitamin E; about 2.4 mg to about 3.6 mg vitamin $B_1$; about 1.6 mg to about 2.4 mg vitamin $B_2$; about 16 mg to about 24 mg vitamin $B_3$; about 8 mg to about 12 mg vitamin $B_5$; about 24 mg to about 36 mg vitamin $B_6$; about 800 µg to about 1200 µg vitamin $B_{12}$; about 240 µg to about 360 µg biotin; about 4.4 mg to about 6.6 mg vitamin $B_9$; about 56 µg to about 84 µg selenium; and about 16 mg to about 24 mg zinc.

In another embodiment, the compositions of the present invention may comprise about 90 mg to about 110 mg vitamin C; about 31.5 IU to about 38.5 IU vitamin E; about 2.7 mg to about 3.3 mg vitamin $B_1$; about 1.8 mg to about 2.2 mg vitamin $B_2$; about 18 mg to about 22 mg vitamin $B_3$; about 9 mg to about 11 mg vitamin $B_5$; about 27 mg to about 33 mg vitamin $B_6$; about 900 µg to about 1100 µg vitamin $B_{12}$; about 270 µg to about 330 µg biotin; about 4.95 mg to about 6.05 mg vitamin $B_9$; about 63 µg to about 77 µg selenium; and about 18 mg to about 22 mg zinc.

In a further particular embodiment of the present invention, the compositions may comprise about 100 mg vitamin C; about 35 IU vitamin E; about 3 mg vitamin $B_1$; about 2 mg vitamin $B_2$; about 20 mg vitamin $B_3$; about 10 mg vitamin $B_5$; about 30 mg vitamin $B_6$; about 12 µg vitamin $B_{12}$; about 300 µg biotin; about 5.5 mg vitamin $B_9$; about 70 µg selenium; and about 20 mg zinc.

The embodiments of the invention just described may be administered to a patient daily. These embodiments may also be administered orally and may comprise pharmaceutically acceptable carriers. It is contemplated that these formulations can be used to treat nutritional deficiencies in patients requiring such treatment due to kidney disease, end-stage renal disease, renal insufficiency, dialysis therapy, dietary restrictions or other disease states that result in increased oxidative stress, elevated cholesterol levels, and/or elevated homocysteine levels.

The present invention also includes methods for supplementing nutritional deficiencies in patients that have nutritional deficiencies due to kidney disease, end-stage renal disease, renal insufficiency, dialysis therapy, dietary restrictions or other disease states that result in increased oxidative stress, elevated cholesterol levels, and/or elevated homocysteine levels. The methods of the present invention may also utilize compositions that can be used as nutritional supplements for patients undergoing dialysis therapy or for patients on a restricted diet. In one embodiment, the methods of the present invention may utilize compositions comprising vitamin C, vitamin E, B-complex vitamins, selenium, and zinc. More specifically, the methods of the present invention may utilize compositions that may comprise vitamin C, vitamin E, vitamin $B_1$, vitamin $B_2$, vitamin $B_3$, vitamin $B_5$, vitamin $B_6$, vitamin $B_{12}$, biotin, vitamin $B_9$, selenium, and zinc.

In one embodiment, the methods of the present invention may utilize compositions that comprise one or more of vitamin C in the form of ascorbic acid; vitamin E in the form of d-alpha tocopheryl succinate or d-alpha tocopheryl acetate; vitamin $B_1$, in the form of thiamine mononitrate; vitamin $B_2$ in the form of riboflavin; vitamin $B_3$ in the form of niacinamide or niacin; vitamin $B_5$ in the form of pantothenic acid (d-calcium pantothenate); vitamin $B_6$ in the form of pyridoxine hydrochloride; vitamin $B_{12}$ in the form of cyanocobalamin; biotin; vitamin $B_9$ in the form of folic acid, folacin, metafolin, folate and/or one or more natural isomers of folate including (6S)-tetrahydrofolic acid or a polyglutamyl derivative thereof, 5-methyl-(6S)-tetrahydrofolic acid or a polyglutamyl derivative thereof, 5-formyl-(6S)-tetrahydrofolic acid or a polyglutamyl derivative thereof, 10-formyl-(6R)-tetrahydrofolic acid or a polyglutamyl derivative thereof, 5,10-methylene-(6R)-tetrahydrofolic acid or a polyglutamyl derivative thereof, 5,10-methenyl-(6R)-tetrahydrofolic acid or a polyglutamyl derivative thereof and 5-formimino-(6S)-tetrahydrofolic acid or a polyglutamyl derivative thereof; selenium in the form of L-selenomethionine; and zinc in the form of L-Optizinc ZML-200 InterHealth∂™ or zinc oxide.

In another embodiment of the present invention, the methods may utilize compositions that may be substantially free of any other added vitamins and minerals not described in the preceding paragraph. For example, the methods of the present invention may utilize compositions that are substantially free of added alpha carotene; substantially free of added beta carotene; substantially free of added lutein; substantially free of added lycopene; substantially free of added zeaxanthin; substantially free of added vitamin $B_4$; substantially free of added vitamin $B_7$; substantially free of added vitamin $B_8$; substantially free of added vitamin $B_{10}$; substantially free of added vitamin $B_{11}$; substantially free of added vitamin D; substantially free of added calcium; substantially free of added chromium; substantially free of added iron; substantially free of added magnesium; substantially free of added copper; substantially free of added manganese; substantially free of added boron; substantially free of added odorless garlic; substantially free of added coenzyme Q-10; substantially free of added 1-carnitine; substantially free of added grape seed extract; substantially free of added green tea extract; substantially free of added quercetin; substantially free of added hawthorne berries; and/or substantially free of added alpha lipoic acid.

In another specific embodiment, the methods of the present invention may utilize compositions that may be substantially free of added vitamin C; substantially free of added vitamin E; substantially free of added vitamin $B_1$; substantially free of added vitamin $B_2$; substantially free of added vitamin $B_3$; substantially free of added vitamin $B_5$; substantially free of added vitamin $B_6$; substantially free of added vitamin $B_{12}$; substantially free of added biotin; substantially free of added vitamin $B_9$; substantially free of added selenium; and/or substantially free of added zinc.

In another embodiment, the methods of the present invention may utilize compositions that may comprise about 60 mg to about 140 mg vitamin C; about 17.5 IU to about 52.5 IU vitamin E; about 1.5 mg to about 4.5 mg vitamin $B_1$; about 1 mg to about 3 mg vitamin $B_2$; about 10 mg to about 30 mg vitamin $B_3$; about 5 mg to about 15 mg vitamin $B_5$; about 18 mg to about 42 mg vitamin $B_6$; about 500 µg to about 1500 µg vitamin $B_{12}$; about 150 µg to about 450 µg biotin; about 3 mg to about 8 mg vitamin $B_9$; about 35 µg to about 105 µg selenium; and about 10 mg to about 30 mg zinc.

In another particular embodiment, the methods may utilize compositions that may comprise about 80 mg to about 120 mg vitamin C; about 28 IU to about 42 IU vitamin E; about 2.4 mg to about 3.6 mg vitamin $B_1$; about 1.6 mg to about 2.4 mg vitamin $B_2$; about 16 mg to about 24 mg vitamin $B_3$; about 8 mg to about 12 mg vitamin $B_5$; about 24 mg to about 36 mg vitamin $B_6$; about 800 µg to about 1200 µg vitamin $B_{12}$; about 240 µg to about 360 µg biotin; about 4.4 mg to about 6.6 mg vitamin $B_9$; about 56 µg to about 84 µg selenium; and about 16 mg to about 24 mg zinc.

In yet another embodiment of the present invention, the methods may utilize compositions that may comprise about 90 mg to about 110 mg vitamin C; about 31.5 IU to about 38.5 IU vitamin E; about 2.7 mg to about 3.3 mg vitamin $B_1$; about 1.8 mg to about 2.2 mg vitamin $B_2$; about 18 mg to about 22 mg vitamin $B_3$; about 9 mg to about 11 mg vitamin $B_5$; about 27 mg to about 33 mg vitamin $B_6$; about 900 µg to about 1100 µg vitamin $B_{12}$; about 270 µg to about 330 µg biotin; about 4.95 mg to about 6.05 mg vitamin $B_9$; about 63 µg to about 77 µg selenium; and about 18 mg to about 22 mg zinc.

In a further particular embodiment, the methods may utilize compositions that may comprise about 100 mg vitamin C; about 35 IU vitamin E; about 3 mg vitamin $B_1$; about 2 mg vitamin $B_2$; about 20 mg vitamin $B_3$; about 10 mg vitamin $B_5$; about 30 mg vitamin $B_6$; about 12 µg vitamin $B_{12}$; about 300 µg biotin; about 5.5 mg vitamin $B_9$; about 70 µg selenium; and about 20 mg zinc.

The methods of the present invention may include administering the compositions of the invention to a patient daily. The methods also contemplate the oral administration of compositions that may comprise pharmaceutically acceptable carriers. It is contemplated that these formulations can be used to treat nutritional deficiencies in patients requiring such treatment due to kidney disease, end-stage renal disease, renal insufficiency, dialysis therapy, dietary restrictions or other disease states. The composition may also be used to treat the nutritional deficiencies of any disease state that results in increased oxidative stress, elevated cholesterol levels, or elevated homocysteine levels.

Other objectives, features and advantages of the present invention will become apparent from the following detailed description. The detailed description and the specific examples, although indicating specific embodiments of the invention, are provided by way of illustration only. Accordingly, the present invention also includes those various changes and modifications within the spirit and scope of the invention that may become apparent to those skilled in the art from this detailed description.

DETAILED DESCRIPTION OF THE INVENTION

It is understood that the present invention is not limited to the particular methodologies, protocols, fillers, excipients, etc . . . , described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a vitamin" is a reference to one or more vitamins and includes equivalents thereof known to those skilled in the art and so forth.

Unless defined otherwise, all technical and scientific terms used herein have the same meanings as commonly understood by one of ordinary skill in the art to which this invention belongs. Specific methods, devices, and materials are described, although any methods and materials similar or equivalent to those described herein can be used in the practice or testing of the present invention.

The nutritional therapy of individuals with renal disease requires a unique formulation due to the multiple metabolic and biochemical changes, as well as dietary restrictions. The prescribed diet restrictions usually result in decreased consumption of vital nutrients such as vitamin C, vitamin E, the B-complex vitamins, and zinc. Rocco et al., 7 J. RENAL NUTR. 17-24 (1997). In addition, patients with end-stage renal disease are often in a uremic state which increases oxidative stress and free radical production, affects the appetite, and alters the body's ability to utilize nutrients. Tetta et al., 17 BLOOD PURIF. 118-126 (1999). The dialysis process may also result in a depletion of essential nutrients. Stein et al., 3 BLOOD PURIF. 52-62 (1985). The novel compositions and related methods of the present invention comprise a unique mixture of vitamins and minerals that are useful as nutritional supplements for treating patients suffering from renal disease.

The term "renal disease" is a generic expression encompassing an array of disorders that afflict the kidneys. The term "renal patient" includes patients suffering from renal disease. In general, renal diseases are categorized according to the affected morphologic component: glomerulus, tubules, and blood vessels. The glomerulus is a network of branching and anastomosing capillaries that filters proteins, toxins, and other substances from the blood. A number of factors may lead to injury to glomeruli including secondary affects from immunologic, vascular, and metabolic diseases. Diseases of the glomerulus include, but are not limited to, glomerulonephritis, nephrotic syndrome, lipoid nephrosis, glomerulosclerosis, Berger disease, and hereditary nephritis. ROBBINS PATHOLOGIC BASIS OF DISEASE 942 (Cotran et al., $6^{th}$ ed. 1999).

The tubules of the kidney reabsorb components from the glomerulus filtrate into the blood. The epithelial cells of the tubules are particularly sensitive to ischemia and toxins and thus, predispose the tubules to injury. Disease conditions of the tubules include, but are not limited to, acute tubular necrosis, tubulointerstitial nephritis, pyelonephritis, urate nephropathy, and nephrocalcinosis. Id. at 968-980.

The richly vascularized kidney receives approximately 25% of the cardiac output and systemic vascular diseases such as vasculitis and hypertension may have secondary effects on renal blood vessels. Other diseases of the renal blood vessels include, but are not limited to, benign nephrosclerosis, renal artery stenosis, thrombotic microangiopathies, hemolytic-uremic syndrome, and sickle cell disease nephropathy. Id. at 981-987. In addition, tumors such as oncocytoma and renal cell carcinoma may also impair renal function. Id. at 991-994. Regardless of the origin, the numerous diseases described above eventually culminate in chronic renal disease and ultimately end-stage renal disease.

Reduced levels of serum vitamin C have been observed in chronic renal failure patients. These reduced levels were most likely due to a low-potassium diet and decreased food intake. Marumo et al., 9 INT. J. ARTIF. ORGANS 17-24 (1986). The low-potassium renal diet generally restricts fruit and vegetables which are abundant in potassium and vitamin C. The major biochemical role of vitamin C is as a cosubstrate in metal catalyzed hydroxylations and it has antioxidant properties interacting directly with superoxide hydroxyl radicals and singlet oxygen. In addition, vitamin C provides antioxidant protection for folate and vitamin E. RECOMMENDED DIETARY ALLOWANCES 115 (National Research Council, $10^{th}$ ed., 1989) (hereinafter "RDA"). In a specific embodiment of the present invention, vitamin C may be included in the form of ascorbic acid. In another specific embodiment, vitamin C may be included in amounts ranging from about 60 mg to about 140 mg. In another specific embodiment, vitamin C may be included in amounts ranging from about 80 mg to about 120 mg. In yet another specific embodiment, vitamin C may be included in amounts ranging from about 90 mg to about 110 mg. In a further embodiment, vitamin C may be included in an amount of about 100 mg.

Vitamin E is an antioxidant found in biological membranes where it protects the phospholipid membrane from oxidative stress. RDA, at 99-101. It is also an antiatherogenic agent and studies have demonstrated a reduced risk of coronary heart disease with increased intake of vitamin E. Stampfer et al., 328 N. ENGL. J. MED. 1444-1449 (1993). Decreased levels of vitamin E have been observed in chronic renal failure patients and in patients undergoing dialysis. Taccone-Gallucci et al., 27 CLIN. NEPHROL. 238-241 (1987); Ito et al., 217 JAMA 699 (1971). In addition, it has been demonstrated that the typical renal diet is deficient in vitamin E. Ono, 40 NEPHRON 440-445 (1985). Furthermore, atherosclerotic cardiovascular disease is a leading cause of death in patients with end-stage renal disease. Maiorca, et al., 43 KIDNEY INT. S4-S10 (1993). In a specific embodiment of the present invention, vitamin E may be included in the form of d-alpha-tocopheryl acetate. In another specific embodiment, vitamin E may be included in the form of an equivalent molar amount of d-alpha tocopheryl succinate. In another specific embodiment, vitamin E may be included in amounts ranging from about 17.5 IU to about 52.5 IU. In another specific embodiment, vitamin E may be included in amounts ranging from about 28 IU to about 42 IU. In yet another specific embodiment, vitamin E may be included in amounts ranging from about 31.5 IU to about 38.5 IU. In a further embodiment, vitamin E may be included in an amount of about 35 IU.

Thiamine (vitamin $B_1$) is a coenzyme for the oxidative decarboxylation of α-ketoacids and for transketolase which is a component of the pentose phosphate pathway. The activity of thiamine is inhibited by folate deficiency and malnutrition. RDA, at 123. Chronic renal failure patients placed on a low protein diet exhibit a thiamine deficiency. Porrini et al., 59 INT. J. VITAM. NUTR. RES. 304-308 (1989). In addition, erythrocyte transketolase activity is impaired in dialysis patients. Descombes et al., 43 KIDNEY INT. 1319-1328 (1993). Hence, to correct for any potential thiamine deficiency in renal patients, vitamin $B_1$ may be included in the form of thiamine mononitrate in a specific embodiment of the present invention. In another specific embodiment of the present invention, vitamin $B_1$ may be included in amounts ranging from about 1.5 mg to about 4.5 mg. In yet another specific embodiment, vitamin $B_1$ may be included in amounts ranging from about 2.4 mg to about 3.6 mg. In another specific embodiment, vitamin $B_1$ may be included in amounts ranging from about 2.7 mg to about 3.3 mg. In a further embodiment, vitamin $B_1$ may be included in an amount of about 3 mg.

Riboflavin (vitamin $B_2$) is a component of two flavin coenzymes, flavin mononucleotide (FMN) and flavin adenine dinucleotide (FAD). These flavoenzymes are involved in a number of oxidation-reduction reactions including the conversion of pyridoxine and niacin. RDA, at 132. Renal patients prescribed a low protein diet demonstrate evidence of riboflavin deficiency. Porrini et al., 59 INT. J. VITAM. NUTR. RES. 304-308 (1989); Stein et al., 3 BLOOD PURIF. 52-62 (1985). Corneal vascularization and dermatitis has also been noted in patients exhibiting riboflavin deficiency. HANDBOOK, at 116. Thus, in a specific embodiment of the present invention, vitamin $B_2$ may be included in the form of riboflavin. In another specific embodiment, vitamin $B_2$ may be included in amounts ranging from about 1 mg to about 3 mg. In another specific embodiment, vitamin $B_2$ may be included in amounts ranging from about 1.6 mg to about 2.4 mg. In another specific embodiment, vitamin $B_2$ may be included in amounts ranging from about 1.8 mg to about 2.2 mg. In another embodiment, vitamin $B_2$ may be included in an amount of about 2 mg.

Nicotinamide adenine dinucleotide (NAD) and NAD phosphate (NADP) are active coenzymes of niacin (vitamin $B_3$). These coenzymes are involved in numerous enzymatic reactions such as glycolysis, fatty acid metabolism, and steroid synthesis. Niacin is also required for the synthesis of pyroxidine, riboflavin, and folic acid. RDA, at 137. Administration of niacin may also produce a reduction in total cholesterol, LDL, and VLDL levels and an increase in HDL cholesterol. Henkin et al., 91 AM. J. MED. 239-246 (1991). A niacin deficiency has been noted in dialysis patients and reduced amounts of niacin have been demonstrated in a low protein renal diet. DeBari et al., 39 AM. J. CLIN. NUTR. 410-415 (1984); Mackenzie et al.,5 PROC. EUR. DIAL. TRANSPLANT. ASSOC. 172-178 (1968). To maintain appropriate niacin levels in renal patients, a specific embodiment of the present invention may include vitamin $B_3$ in the form of niacin. In another specific embodiment, the present invention may include an equivalent molar amount of niacinamide. In another specific embodiment, vitamin $B_3$ may be included in amounts ranging from about 10 mg to about 30 mg. In another specific embodiment, vitamin $B_3$ may be included in amounts ranging from about 16 mg to about 24 mg. In another specific embodiment, vitamin $B_3$ may be included in amounts ranging from about 18 mg to about 22 mg. In another embodiment, vitamin $B_3$ may be included in an amount of about 20 mg.

Pantothenic acid (vitamin $B_5$) is a component of the coenzyme A macromolecule which is required for the synthesis of fatty acids, cholesterol, steroid hormones, and neurotransmitters. The coenzyme A complex also has a major role in the acetylation and acylation of numerous proteins. RDA, at 169. Low protein diets as typically prescribed for renal patients provide a minimum amount of pantothenic acid. In addition, a decrease in pantothenic acid plasma levels has been observed in dialysis patients. Mackenzie et al. 5 PROC. EUR. DIAL. TRANSPLANT. ASSOC. 172-178 (1968). Therefore, to minimize a deficiency of pantothenic acid in renal patients, vitamin $B_5$ may be included in the form of d-calcium pantothenate. In another specific embodiment, vitamin $B_5$ may be included in amounts ranging from about 5 mg to about 15 mg. In another specific embodiment, vitamin $B_5$ may be included in amounts ranging from about 8 mg to about 12 mg. In another specific embodiment, vitamin $B_5$ may be included in amounts ranging from about 9 mg to about 11 mg. In another embodiment, vitamin $B_5$ may be included in an amount of about 10 mg.

The active forms of pyridoxine (vitamin $B_6$), pyridoxal-5'-phosphate (PLP) and pyridoxamine-5'-phosphate, are coenzymes for numerous enzymes and as such, are essential for gluconeogenesis, niacin formation, and erythrocyte metabolism. RDA, at 142-143. A high incidence of pyridoxine deficiency has been noted in both adult and pediatric chronic renal failure patients, as well as patients undergoing dialysis. Stein et al., 3 BLOOD PURIF. 52-62 (1985); Stockberger et al., 7 NUTR. RES. 1021-1030 (1987); Descombes et al., 43 KIDNEY INT. 1319-1328 (1993). Low protein diets generally have minimal amounts of pyridoxine. Kopple et al., 19 KIDNEY INT. 694-704 (1981). A deficiency in pyridoxine may be attributed to the suppressed immune function observed in chronic renal patients, as well as the increased plasma and tissue oxalate concentrations in renal failure. Dobblestein et al., 5 KIDNEY INT. 233-239 (1974); Morgan et al., 46 NEPHRON 253-257 (1987).

In addition, it has been suggested that pyridoxine deficiency plays a role in homocysteinemia which has been observed in renal patients. Pyridoxine is a coenzyme for both cystathionine synthase and cystathionase, enzymes that catalyze the formation of cysteine from methionine. Homocysteine is an intermediate in this process and elevated levels of plasma homocysteine are recognized as a risk factor for vascular disease. Robinson et al., 94 CIRCULATION 2743-2748 (1996). However, it has been proposed that administration of pyridoxine may reduce the levels of homocysteine. Bostom et al., 49 KIDNEY INT. 147-152 (1996). Hence, in a specific embodiment of the present invention, vitamin $B_6$ may be included in the form of pyridoxine hydrochloride. In another specific embodiment, vitamin $B_6$ may be included in amounts ranging from about 18 mg to about 42 mg. In another specific embodiment, vitamin $B_6$ may be included in amounts ranging from about 24 mg to about 36 mg. In another specific embodiment, vitamin $B_6$ may be included in amounts ranging from about 27 mg to about 33 mg. In yet another embodiment, vitamin $B_6$ may be included in an amount of about 30 mg.

Cyanocobalamin (vitamin $B_{12}$) is the pharmaceutical form of cobalamin which can be converted to the active coenzymes, methylcobalamin and 5'-deoxyadenosylcobalamin. These coenzymes are necessary for folic acid metabolism, conversion of coenzyme A, and myelin synthesis. For example, methylcobalamin catalyzes the demethylation of a folate cofactor which is involved in DNA synthesis. A lack of demethylation may result in folic acid deficiency. RDA, at 159-160. Further, vitamin $B_{12}$ is necessary for folic acid delivery to tissues. RDA, at 150. A deficiency of vitamin $B_{12}$ has been observed in chronic renal failure patients and dialysis patients. In addition, slow nerve conduction velocities have also been noted in dialysis patients. Rostand, 29 AM. J. CLIN. RES. 691-697 (1976). Based on these observations, vitamin $B_{12}$ supplementation may be appropriate as a means to compensate for any deficiency. Furthermore, since vitamin $B_{12}$ has a role in folic acid metabolism, supplementation may be effective in managing homocysteine levels in renal patients. Thus, in one specific embodiment of the present invention, vitamin $B_{12}$ may be included in the form of cyanocobalamin. In another specific embodiment, vitamin $B_{12}$ may be included in amounts ranging from about 500 µg to about 1500 µg. In another specific embodiment, vitamin $B_{12}$ may be included in amounts ranging from about 800 µg to about 1200 µg. In another specific embodiment, vitamin $B_{12}$ may be included in amounts ranging from about 900 µg to about 1100 µg. In a further embodiment, vitamin $B_{12}$ may be included in an amount of about 1000 µg.

Biotin acts a coenzyme for a number of carboxylases and thus, has an important role in gluconeogenesis, fatty acid metabolism, and amino acid metabolism. RDA, at 166. It has been shown that biotin inhibits the effects of uremic toxins on tubulin polymerizaton. Braguer et al., 57 NEPHRON 192-196 (1991). Furthermore, there is some evidence to suggest that chronic renal failure patients and dialysis patients are at a risk for the development of a biotin deficiency. Mackenzie et al., 5 PROC. EUR. DIAL. TRANSPLANT. ASSOC. 172-178 (1968). In several dialysis patients diagnosed with uremic encephalopathy and neuropathy, symptoms of these disorders were alleviated by administration of biotin. Yatzidis et al., 305 N. ENGL. J. MED. 764 (1981). In a specific embodiment of the present invention, biotin may be included in amounts ranging from about 150 µg to about 450 µg. In another specific embodiment of the present invention, biotin may be included in amounts ranging from about 240 µg to about 360 µg. In a further specific embodiment of the present invention, biotin may be included in amounts ranging from about 270 µg to about 330 µg. In another embodiment, biotin may be included in an amount of about 300 µg.

Folic acid (vitamin $B_9$), in its active form, tetrahydrofolate, is a coenzyme that is involved in the transfer of methyl groups and it plays a role in DNA synthesis, purine synthesis, and amino acid synthesis, such as the conversion of glycine to serine and the transformation of homocysteine to methionine. The metabolism of folic acid is altered by uremia and the absorption of tetrahydrofolate is impaired in chronic renal failure patients. Said et al., 6 ACTA VITAMINOL. ENZYMOL. 339-346 (1984). Furthermore, the diet generally prescribed for renal patients tends to be low in folic acid content and medications used by chronic renal failure patients may also inhibit the activity of folic acid. Stein et al., 3 BLOOD PURIF. 52-62 (1985); Cunningham et al., 282 BR. MED. J. 1582 (1981). The high incidence of homocysteinemia observed in chronic renal failure patients and the related risk of development of atherosclerosis suggest that folic acid supplementation may provide an effective method for managing this condition and also provide a cardio-protective effect. Robinson et al., 94 CIRCULATION 2743-2748 (1996). Therefore, in a specific embodiment of the present invention, vitamin $B_9$ may be included in the form of folic acid. In another embodiment, vitamin $B_9$ may be included in the forms of folic acid, folacin, metafolin, folate and/or one or more natural isomers of folate including (6S)-tetrahydrofolic acid or a polyglutamyl derivative thereof, 5-methyl-(6S)-tetrahydrofolic acid or a polyglutamyl derivative thereof, 5-formyl-(6S)-tetrahydrofolic acid or a polyglutamyl derivative thereof, 10-formyl-(6R)-tetrahydrofolic acid or a polyglutamyl derivative thereof, 5,10-methylene-(6R)-tetrahydrofolic acid or a polyglutamyl derivative thereof, 5,10-methenyl-(6R)-tetrahydrofolic acid or a polyglutamyl derivative thereof and 5-formimino-(6S)-tetrahydrofolic acid or a polyglutamyl derivative thereof. In another specific embodiment, vitamin $B_9$ may be included in amounts ranging from about 3 mg to about 8 mg. In another specific embodiment, vitamin $B_9$ may be included in amounts ranging from about 4.4 mg to about 6.6 mg. In another specific embodiment, vitamin $B_9$ may be included in amounts ranging from about 4.95 mg to about 6.05 mg. In another embodiment, vitamin $B_9$ may be included in an amount of about 5.5 mg.

Selenium is a component of the antioxidant enzyme, glutathione peroxidase, which plays a critical role in the control of oxygen metabolism, particularly catalyzing the breakdown of hydrogen peroxide. Burk, 3 ANNU. REV. NUTR. 53-70 (1983). Glutathione peroxidase prevents the generation of free radicals and decreases the risk of oxidative damage to numerous tissues, including the vascular system. Holben, 99 J. AM. DIET. ASSOC. 836-843 (1999). Diabetic patients have even higher levels of oxidative stress due to the combination of diabetes and renal disease. Kedziora-Kornatowska, et al., 11 NEPHROL. DIAL. TRANSPLANT. 2829-2832 (1998). Selenium may be lost during dialysis therapy and dietary selenium may be less than adequate due to protein restrictions. Several studies have demonstrated significant decreases in serum selenium, selenium-dependent enzymes, and increased lipid peroxidation in dialysis patients. Smith et al., 7 J. RENAL NUTR. 69-72 (1997); Zima et al., 16 BLOOD PURIF. 253-260 (1998). Oral and intravenous selenium supplementation has proven to be effective in improving the selenium status and immune function of renal patients, while decreasing the levels of oxidative stress products. Temple et al., 10 J. RENAL NUTR. 16 (2000). Therefore, in one embodiment of the present invention, the compositions may comprise selenium in the form of L-selenomethionine. In another specific embodiment, selenium may be included in amounts ranging from about 35 μg to about 105 μg. In another specific embodiment, selenium may be included in amounts ranging from about 56 μg to about 84 μg. In another specific embodiment, selenium may be included in amounts ranging from about 63 μg to about 77 μg. In another embodiment, selenium may be included in an amount of about 70 μg.

There are more than 200 zinc metalloenzymes including aldolase, alcohol dehydrogenase, RNA polymerase, and protein kinase C. Thus, zinc plays a role in numerous metabolic activities such as nucleic acid production, protein synthesis, and development of the immune system. Zima et al., 17 BLOOD PURIF. 182-186 (1999). Several studies have shown decreased serum levels of zinc in dialysis patients and patients with renal failure. Thomson et al., 23 KIDNEY INT. 9-14 (1983); Muirhead et al., 6 AM. J. NEPHROL. 422-426 (1986). Zinc supplementation has been shown to improve a number of clinical symptoms observed in renal patients such as dygeusia, nerve conduction velocity, and impotency, and it has been proposed that zinc supplementation may restore impaired cell-mediated immunity and lymphocyte function. Zima et al., 17 BLOOD PURIF. 182-186 (1999). In a specific embodiment of the present invention, zinc may be included in the form of L-Optizinc ZML-200 InterHealth9™. In another specific embodiment, zinc may be included in amounts ranging from about 10 mg to about 30 mg. In another specific embodiment, zinc may be included in amounts ranging from about 16 mg to about 24 mg. In another embodiment, zinc may be included in amounts ranging from about 18 mg to about 22 mg. In yet another embodiment, zinc may be included in an amount of about 20 mg.

The compositions of the present invention are preferably administered in amounts to patients that provide the supplementation required to alleviate the vitamin and mineral deficiencies associated with renal disease. A preferred dosage of the compositions of the present invention may consist of one or more caplets for human oral consumption. If more than one caplet is used, each individual caplet may be identical to the other caplets, or each may contain only some of the ingredients of the composition, so that the combination of the different caplets comprises a composition of the present invention.

The compositions of the present invention represent a combination of essential vitamins and minerals that work together with various metabolic systems and physiological responses of the human body. The ingredients of the present invention are preferably combined into a composition which may be in the form of a solid powder, caplets, tablets, lozenges, pills, capsules, or a liquid, and which may be administered alone or in suitable combination with other components. For example, the composition of the present invention may be administered in one or more caplets or lozenges as practical for ease of administration. Each of the vitamins and minerals is commercially available, and can be blended to form a single composition or can form multiple compositions which may be co-administered.

To prepare the components of the present invention, each of the active ingredients may be combined in intimate admixture with a suitable carrier according to conventional compounding techniques. This carrier may take a wide variety of forms depending upon the form of the preparation desired for administration, e.g., oral, sublingual, nasal, topical patch, or parenteral. The composition may comprise one to three caplets or lozenges, the composition of each being identical to each other caplet or lozenge.

In preparing the composition in oral dosage form, any of the usual media may be utilized. For liquid preparations (e.g., suspensions, elixirs, and solutions) media containing for example water, oils, alcohols, flavoring agents, preservatives, coloring agents and the like may be used. Carriers such as starches, sugars, diluents, granulating agents, lubricants, binders, disintegrating agents and the like may be used to prepare oral solids (e.g., powders, caplets, pills, tablets, capsules, and lozenges). Controlled release forms may also be used. Because of their ease in administration, caplets, tablets, pills, and capsules represent the most advantageous oral dosage until form, in which case solid carriers are employed. If desired, tablets may be sugar coated or enteric coated by standard techniques.

The invention will be further illustrated by the following non-limiting examples.

EXAMPLE 1

A composition of the following formulation was prepared in caplet form by standard methods known to those skilled in the art:

| Ascorbic acid | 100 mg |
| d-Alpha Tocophenyl Succinate | 35 IU |
| Thiamine Mononitrate | 3 mg |
| Riboflavin | 2 mg |
| Niacin | 20 mg |
| d-Calcium Pantothenate | 10 mg |
| Pyridoxine Hydrochloride | 30 mg |
| Cyanocobalamin | 1000 μg |
| Biotin | 30 μg |
| Folic acid | 5.5 mg |
| L-Selenomethionine | 70 μg |
| L-Optizinc ZML-200 Inter-Health ™ | 20 mg |

One (1) caplet per day is the recommended dosage or as recommended by physician.

EXAMPLE 2

A study is undertaken to evaluate the effectiveness of the composition of the present invention in the treatment of patients diagnosed with end-stage renal disease (ESRD). The objective of the study is to determine whether oral intake of the composition results in an improvement of the nutritional status of the patient.

A double-blind, placebo controlled study is conducted over a twelve-month period. A total of sixty subjects (30 men and 30 women) aged 40 to 85 years, suffering from ESRD, are chosen for the study. An initial assessment of nutritional status is conducted. Vitamin C, selenium and zinc levels are measured using spectrophotometric and colorimetric methods. Vitamin $B_9$ and vitamin $B_{12}$ levels are measured by radio-immunoassay. Biotin and vitamin $B_6$ levels are assessed by high performance liquid chromatography and vitamin $B_3$ levels are determined by measuring urinary excretion of N'methylnicotinamide and its pyridine. Vitamin E is measured by the peroxide hemolysis test and vitamin $B_1$ is measured by determining erythrocyte transketolase activity. Vitamin $B_2$ levels are assessed by examining erythrocyte glutathione reductase activity and vitamin $B_5$ by measuring coenzyme A activity.

The sixty subjects are separated into two separate groups of fifteen men and fifteen women. In the first group, each subject is administered 1 to 2 caplets, daily, of the composition as described in example 1. In the second group (control) each subject is administered 1 to 2 placebo caplets, daily.

An assessment of nutritional status for each subject is measured at one-month intervals for a twelve month period as described above and the data is evaluated using multiple linear regression analysis and a standard students t-test. In each analysis the baseline value of the outcome variable is included in the model as a covariant. Treatment by covariant interaction effects is tested by the method outlined by Weigel & Narvaez, 12 CONTROLLED CLINICAL TRIALS 378-94 (1991). If there are no significant interaction effects, the interaction terms are removed from the model. The regression model assumptions of normality and homogeneity of variance of residuals are evaluated by inspection of the plots of residuals versus predicted values. Detection of the temporal onset of effects is done sequentially by testing for the presence of significant treatment effects at 18, 12, and 6 weeks, proceeding to the earlier time in sequence only when significant effects have been identified at each later time period. Changes from the baseline within each group are evaluated using paired t-tests. In addition, analysis of variance is performed on all baseline measurements and measurable subject characteristics to assess homogeneity between groups. All statistical procedures are conducted using the Statistical Analysis System (SAS Institute Inc., Cary, N.C.). An alpha level of 0.05 is used in all statistical tests.

A statistically significant improvement in the nutritional status is observed in the treated subjects upon completion of the study but not the controls. The differences between nutritional state in the treated subjects and controls are statistically significant. Therefore, the study confirms that oral administration of the composition of the present invention is effective in the treatment of patients diagnosed with ESRD.

The disclosures of all references and publications cited above are expressly incorporated by reference in their entireties to the same extent as if each were incorporated by reference individually. Various modifications and variations of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the art, are intended to be within the scope of the following claims.

We claim:

1. A composition consisting of vitamin C, vitamin E, vitamin $B_1$, vitamin $B_2$, vitamin $B_3$, vitamin $B_5$, vitamin $B_6$, vitamin $B_{12}$, biotin, vitamin $B_9$, selenium, zinc and one or more pharmaceutically acceptable carriers.

2. The composition of claim 1, wherein said composition consists of about 60 mg to about 140 mg vitamin C; about 17.5 IU to about 52.5 IU vitamin E; about 1.5 mg to about 4.5 mg vitamin $B_1$; about 1 mg to about 3 mg vitamin B2; about 10mg to about 30 mg vitamin $B_3$; about 5 mg to about 15 mg vitamin $B_5$; about 18 mg to about 42 mg vitamin $B_6$; about 500 µg to about 1500 µg vitamin $B_{12}$; about 150 µg to about 450 µg biotin; about 3 mg to about 8 mg vitamin $B_9$; about 35 µg to about 105 µg selenium; about 10 mg to about 30 mg zinc and one or more pharmaceutically acceptable carriers.

3. The composition of claim 1, wherein said composition consists of 100 mg vitamin C; about 35 IU vitamin E; about 3 mg vitamin $B_1$; about 2 mg vitamin $B_2$; about 20 mg vitamin $B_3$; about 10 mg vitamin $B_5$; about 30 mg vitamin $B_6$; about 1.0 mg vitamin $B_{12}$; about 300 µg biotin; about 5.5 mg vitamin $B_9$; about 70 µg selenium; about 20 mg zinc and one or more pharmaceutically acceptable carriers.

4. A method consisting of administering to a patient the composition of claim 1.

5. The method of claim 4, wherein said composition consists of about 60 mg to about 140mg vitamin C; about 17.5 IU to about 52.5 IU vitamin E; about 1.5 mg to about 4.5 mg vitamin $B_1$; about 1 mg to about 3 mg vitamin $B_2$; about 10 mg to about 30 mg vitamin $B_3$; about 5 mg to about 15 mg vitamin $B_5$; about 18 mg to about 42 mg vitamin $B_6$; about 500 µg to about 1500 µg vitamin $B_{12}$; about 150 µg to about 450 µg biotin; about 3 mg to about 8 mg vitamin $B_9$; about 35 µg to about 105 µg selenium; and about 10 mg to about 30 mg zinc and one or more of a pharmaceutically acceptable carrier.

6. The method of claim 4, wherein said composition consists of 100 mg vitamin C; about 35 IU vitamin E; about 3 mg vitamin $B_1$; about 2 mg vitamin $B_2$; about 20 mg vitamin $B_3$; about 10 mg vitamin $B_5$; about 30 mg vitamin $B_6$; about 1.0 mg vitamin $B_{12}$; about 300 µg biotin; about 5.5 mg vitamin $B_9$; about 70 µg selenium; and about 20 mg zinc and one or more of a pharmaceutically acceptable carrier.

* * * * *